(12) United States Patent
Neumann

(10) Patent No.: US 10,857,426 B1
(45) Date of Patent: Dec. 8, 2020

(54) METHODS AND SYSTEMS FOR GENERATING FITNESS RECOMMENDATIONS ACCORDING TO USER ACTIVITY PROFILES

(71) Applicant: KPN Innovations, LLC, Lakewood, CO (US)

(72) Inventor: Kenneth Neumann, Lakewood, CO (US)

( * ) Notice: Subject to any disclaimer, the term of this patent is extended or adjusted under 35 U.S.C. 154(b) by 0 days.

(21) Appl. No.: 16/699,400

(22) Filed: Nov. 29, 2019

(51) Int. Cl.
| | |
|---|---|
| *A63B 24/00* | (2006.01) |
| *G16H 50/20* | (2018.01) |
| *G06K 9/62* | (2006.01) |
| *G06N 20/00* | (2019.01) |
| *G06F 16/9035* | (2019.01) |
| *G16H 20/30* | (2018.01) |

(52) U.S. Cl.
CPC ...... *A63B 24/0062* (2013.01); *G06F 16/9035* (2019.01); *G06K 9/6218* (2013.01); *G06K 9/6276* (2013.01); *G06N 20/00* (2019.01); *G16H 20/30* (2018.01); *G16H 50/20* (2018.01); *A63B 2024/0065* (2013.01)

(58) Field of Classification Search
CPC ...... G16H 20/30; G16H 50/20; G06K 9/6218; G06K 9/6276; G06F 16/9035; G06N 20/00; A63B 24/0062; A63B 2024/0065
See application file for complete search history.

(56) References Cited

U.S. PATENT DOCUMENTS

| | | | |
|---|---|---|---|
| 9,474,934 B1 | 10/2016 | Krueger et al. | |
| 9,704,412 B2 | 7/2017 | Wells et al. | |
| 9,848,823 B2 | 12/2017 | Raghuram et al. | |
| 2015/0294595 A1 | 10/2015 | Hu et al. | |
| 2016/0262693 A1 | 9/2016 | Sheon | |
| 2017/0061817 A1 | 3/2017 | Mettler May | |
| 2017/0100637 A1 | 4/2017 | Princen et al. | |
| 2017/0266501 A1* | 9/2017 | Sanders | A43B 3/0005 |
| 2018/0090229 A1* | 3/2018 | Sanyal | H04L 67/30 |
| 2018/0133551 A1 | 5/2018 | Chang et al. | |
| 2018/0330810 A1* | 11/2018 | Gamarnik | G16H 20/30 |
| 2018/0342323 A1* | 11/2018 | Shankar | G06N 3/0427 |

(Continued)

FOREIGN PATENT DOCUMENTS

WO   2019075185   4/2019

OTHER PUBLICATIONS

"Heart Rate Monitoring, Activity Recognition, and Recommendation for E-Coaching"; Pessemier & Martens; Sep. 2008; https://biblio.ugent.be/download/8572386/8572388.pdf.

(Continued)

*Primary Examiner* — Sundhara M Ganesan

(74) *Attorney, Agent, or Firm* — Caldwell Intellectual Propert

(57) ABSTRACT

A system for generating fitness recommendations according to user activity profiles. The system includes a computing device configured to retrieve an element of user activity data and an element of user physiological data. A computing device generates utilizing fitness training data in combination with classification algorithms and a fitness classifier an output that includes a fitness profile. A computing device utilizes feature learning algorithms combined with a fitness profile to identify recommended exercises.

18 Claims, 6 Drawing Sheets

(56) References Cited

U.S. PATENT DOCUMENTS

2018/0361203 A1* 12/2018 Wang ................. A63B 24/0075
2019/0209022 A1    7/2019 Sobol et al.

OTHER PUBLICATIONS

"Gymwatch Launches the First Fitness Tracker to Measure Both Strength and Motion and Offer Real-Time Feedback on Every Type of Exercise"; Business Wire; Nov. 11, 2014; https://www.businesswire.com/news/home/20141111006152/en/GYMWATCH-Launches-Fitness-Tracker-Measure-Strength-Motion.

* cited by examiner

METHODS AND SYSTEMS FOR GENERATING FITNESS RECOMMENDATIONS ACCORDING TO USER ACTIVITY PROFILES

FIELD OF THE INVENTION

The present invention generally relates to the field of artificial intelligence. In particular, the present invention is directed to methods and systems for generating fitness recommendations according to user activity data.

BACKGROUND

Adequate practice of exercises designed to enhance one's longevity can be challenging. Frequently, consumers are overloaded about the latest fitness trends often involving expensive equipment and offering very little health benefits. Selection of exercises unique to each individual on a micromolecular level remains to be seen.

SUMMARY OF THE DISCLOSURE

In an aspect, a system for generating fitness recommendations according to user activity profiles, the system comprising a computing device, the computing device further configured to retrieve from a biological database a user activity profile wherein the user activity profile further comprises a biological extraction and at least an element of user activity data wherein the biological extraction further comprises at least an element of user physiological data. The system further configured to generate using fitness training data wherein fitness training data further comprises a plurality of activity profiles and a plurality of correlated fitness profiles, and using a classification algorithm, a fitness classifier, wherein the fitness classifier inputs activity profiles and outputs fitness profiles. The system further configured to calculate using the fitness classifier a classification algorithm utilizing the user activity profile as an input and output a selected fitness profile utilizing the fitness training data. The system further configured to select using the selected fitness profile an activity training set wherein the activity training set includes a plurality of fitness profiles and a plurality of correlated fitness recommendations. The system further configured to generate using the activity training set and the selected fitness profile a feature learning algorithm wherein the feature learning algorithm inputs the selected fitness profile and outputs recommended exercise. The system further configured to identify recommended exercises utilizing the user activity profile.

In an aspect, a method of generating fitness recommendations according to user activity profiles, the method comprising retrieving by a computing device from a biological database a user activity profile wherein the user activity profile further comprises a biological extraction and at least an element of user activity data wherein the biological extraction further comprises at least an element of user physiological data. The method includes generating by the computing device using fitness training data wherein fitness training data further comprises a plurality of activity profiles and a plurality of correlated fitness profiles, and using a classification algorithm, a fitness classifier, wherein the fitness classifier inputs activity profiles and outputs fitness profiles. The method includes calculating by the computing device using the fitness classifier a classification algorithm utilizing the user activity profile as an input and output a selected fitness profile utilizing the fitness training data. The method includes selecting by the computing device using the selected fitness profile an activity training set wherein the activity training set includes a plurality of fitness profiles and a plurality of correlated fitness recommendations. The method includes generating by the computing device using the activity training set and the selected fitness profile a feature learning algorithm wherein the feature learning algorithm inputs the selected fitness profile and outputs recommended exercise. The method includes identifying by the computing device recommended exercises utilizing the user activity profile.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

At a high level, aspects of the present disclosure are directed to systems and methods for generating fitness recommendations according to user activity profiles. In an embodiment, a computing device is configured utilize a biological extraction and an element of user activity data in conjunction with fitness training data and a classification algorithm to select a fitness profile. A fitness profile is utilized in conjunction with activity training data and a feature learning algorithm to generate recommended exercises.

Figure 1:
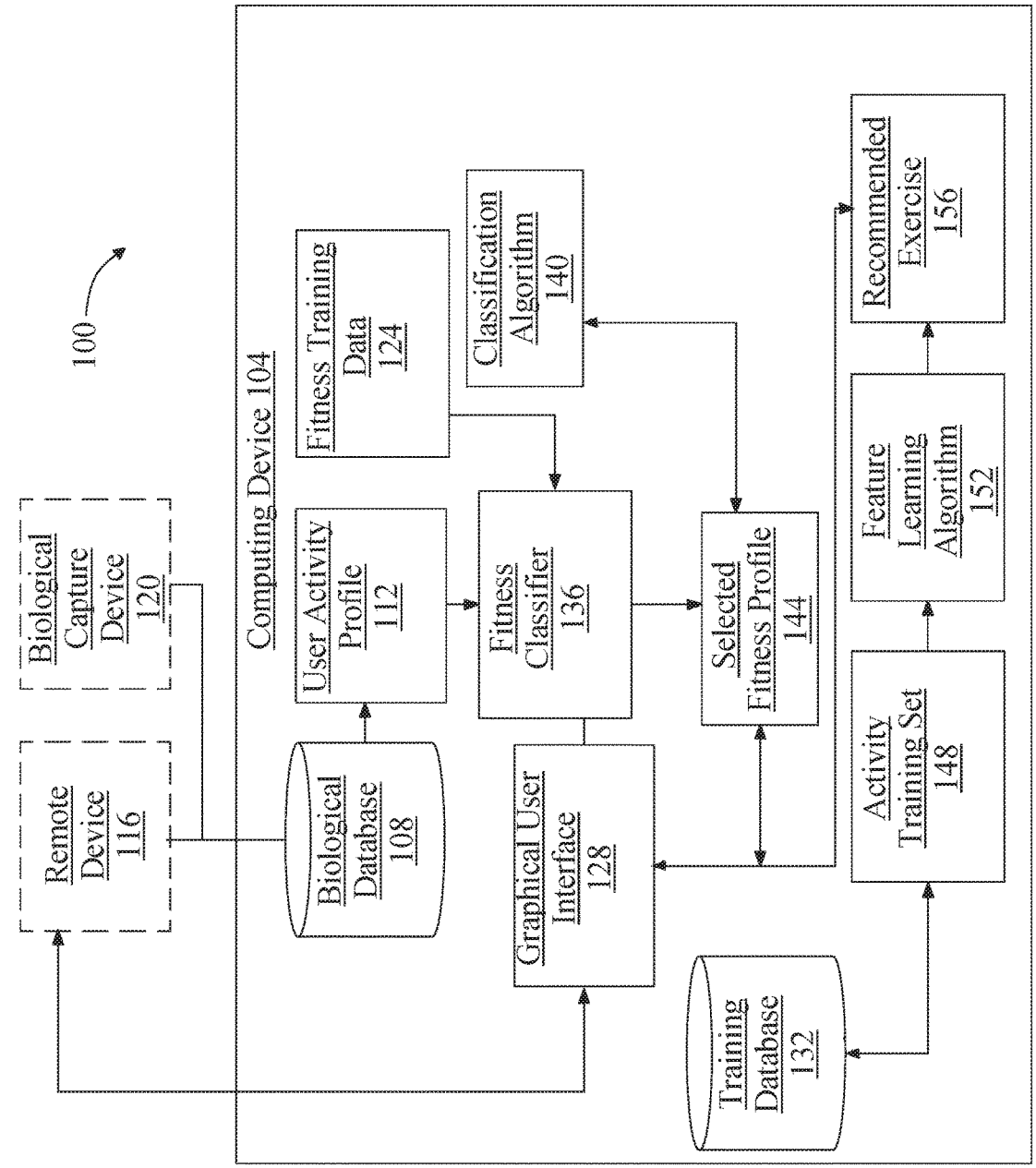
FIG. 1 is a block diagram illustrating an exemplary embodiment of a system for generating fitness recommendations according to user activity profiles.

Referring now to FIG. 1, an exemplary embodiment of a system 100 for generating fitness recommendations according to user activity profile. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker; in an embodiment, this may enable scalability of system 100 and/or computing device 104.

Still referring to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to retrieve from a biological database a user activity profile. Biological database 108 may be implemented, without limitation, as a relational database, a key-value retrieval datastore such as a NOSQL database, or any other format or structure for use as a datastore that a person skilled in the art would recognize as suitable upon review of the entirety of this disclosure. Biological database 108 may be configured to store one or more user activity profiles 112. A "user activity profile" as used in this disclosure, includes one or more data entries describing information pertaining to a user. A user activity profile includes a biological extraction and at least an element of user activity data. A "biological extraction" as used in this disclosure, includes a plurality of user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, a "biological extraction" as used in this disclosure includes at least an element of user physiological data. As used in this disclosure, "physiological data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss.

With continued reference to FIG. 1, physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin Al-C(HbAlc) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibrinogen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing modules as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, and/or on prognostic labels and/or ameliorative processes as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive.

With continued reference to FIG. 1, physiological data may include, without limitation any result of any medical test, physiological assessment, cognitive assessment, psychological assessment, or the like. System 100 may receive at least a physiological data from one or more other devices after performance; system 100 may alternatively or additionally perform one or more assessments and/or tests to obtain at least a physiological data, and/or one or more portions thereof, on system 100. For instance, at least physiological data may include or more entries by a user in a form or similar graphical user interface object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a physiological data and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, physiological data may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure.

With continued reference to FIG. 1, physiological data may include one or more user body measurements. A "user body measurement" as used in this disclosure, includes a measurable indicator of the severity, absence, and/or presence of a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance and without limitation, internal dysfunction of the immune system may produce a variety of different diseases including immunodeficiency, hypersensitivity, allergies, and/or autoimmune disorders.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

With continued reference to FIG. 1, gut-wall, as used herein, includes the space surrounding the lumen of the gastrointestinal tract that is composed of four layers including the mucosa, submucosa, muscular layer, and serosa. The mucosa contains the gut epithelium that is composed of goblet cells that function to secrete mucus, which aids in lubricating the passage of food throughout the digestive tract. The goblet cells also aid in protecting the intestinal wall from destruction by digestive enzymes. The mucosa includes villi or folds of the mucosa located in the small intestine that increase the surface area of the intestine. The villi contain a lacteal, that is a vessel connected to the lymph system that aids in removal of lipids and tissue fluids. Villi may contain microvilli that increase the surface area over which absorption can take place. The large intestine lack villi and instead a flat surface containing goblet cells are present.

With continued reference to FIG. 1, gut-wall includes the submucosa, which contains nerves, blood vessels, and elastic fibers containing collagen. Elastic fibers contained within the submucosa aid in stretching the gastrointestinal tract with increased capacity while also maintaining the shape of the intestine. Gut-wall includes muscular layer which contains smooth muscle that aids in peristalsis and the movement of digested material out of and along the gut. Gut-wall includes the serosa which is composed of connective tissue and coated in mucus to prevent friction damage from the intestine rubbing against other tissue. Mesenteries are also found in the serosa and suspend the intestine in the abdominal cavity to stop it from being disturbed when a person is physically active.

With continued reference to FIG. 1, gut-wall body measurement may include data describing one or more test results including results of gut-wall function, gut-wall integrity, gut-wall strength, gut-wall absorption, gut-wall permeability, intestinal absorption, gut-wall barrier function, gut-wall absorption of bacteria, gut-wall malabsorption, gut-wall gastrointestinal imbalances and the like.

With continued reference to FIG. 1, gut-wall body measurement may include any data describing blood test results of creatinine levels, lactulose levels, zonulin levels, and mannitol levels. Gut-wall body measurement may include blood test results of specific gut-wall body measurements including d-lactate, endotoxin lipopolysaccharide (LPS) Gut-wall body measurement may include data breath tests measuring lactulose, hydrogen, methane, lactose, and the like. Gut-wall body measurement may include blood test results describing blood chemistry levels of albumin, bilirubin, complete blood count, electrolytes, minerals, sodium, potassium, calcium, glucose, blood clotting factors, With continued reference to FIG. 1, gut-wall body measurement may include one or more stool test results describing presence or absence of parasites, *firmicutes, Bacteroidetes*, absorption, inflammation, food sensitivities. Stool test results may describe presence, absence, and/or measurement of acetate, aerobic bacterial cultures, anerobic bacterial cultures, fecal short chain fatty acids, beta-glucuronidase, cholesterol, chymotrypsin, fecal color, *cryptosporidium* EIA, *Entamoeba histolytica*, fecal lactoferrin, *Giardia lamblia* EIA, long chain fatty acids, meat fibers and vegetable fibers, mucus, occult blood, parasite identification, phospholipids, propionate, putrefactive short chain fatty acids, total fecal fat, triglycerides, yeast culture, n-butyrate, pH and the like.

With continued reference to FIG. 1, gut-wall body measurement may include one or more stool test results describing presence, absence, and/or measurement of microorganisms including bacteria, archaea, fungi, protozoa, algae, viruses, parasites, worms, and the like. Stool test results may contain species such as *Bifidobacterium* species, *campylobacter* species, *Clostridium difficile, cryptosporidium* species, *Cyclospora cayetanensis, Cryptosporidium* EIA, *Dientamoeba fragilis, Entamoeba histolytica, Escherichia coli, Entamoeba histolytica, Giardia, H. pylori, Candida albicans, Lactobacillus* species, worms, macroscopic worms, mycology, protozoa, Shiga toxin *E. coli*, and the like.

With continued reference to FIG. 1, gut-wall body measurement may include one or more microscopic ova exam results, microscopic parasite exam results, protozoan polymerase chain reaction test results and the like. Gut-wall body measurement may include enzyme-linked immunosorbent assay (ELISA) test results describing immunoglobulin G (Ig G) food antibody results, immunoglobulin E (Ig E) food antibody results, Ig E mold results, IgG spice and herb results. Gut-wall body measurement may include measurements of calprotectin, eosinophil protein x (EPX), stool weight, pancreatic elastase, total urine volume, blood creatinine levels, blood lactulose levels, blood mannitol levels.

With continued reference to FIG. 1, gut-wall body measurement may include one or more elements of data describing one or more procedures examining gut including for example colonoscopy, endoscopy, large and small molecule challenge and subsequent urinary recovery using large molecules such as lactulose, polyethylene glycol-3350, and small molecules such as mannitol, L-rhamnose, polyethyleneglycol-400. Gut-wall body measurement may include data describing one or more images such as x-ray, MRI, CT scan, ultrasound, standard barium follow-through examination, barium enema, barium with contract, MRI fluoroscopy, positron emission tomography 9PET), diffusion-weighted MRI imaging, and the like.

With continued reference to FIG. 1, microbiome, as used herein, includes ecological community of commensal, symbiotic, and pathogenic microorganisms that reside on or within any of a number of human tissues and biofluids. For example, human tissues and biofluids may include the skin, mammary glands, placenta, seminal fluid, uterus, vagina, ovarian follicles, lung, saliva, oral mucosa, conjunctiva, biliary, and gastrointestinal tracts. Microbiome may include for example, bacteria, archaea, protists, fungi, and viruses. Microbiome may include commensal organisms that exist within a human being without causing harm or disease. Microbiome may include organisms that are not harmful but rather harm the human when they produce toxic metabolites such as trimethylamine. Microbiome may include pathogenic organisms that cause host damage through virulence factors such as producing toxic by-products. Microbiome may include populations of microbes such as bacteria and yeasts that may inhabit the skin and mucosal surfaces in various parts of the body. Bacteria may include for example *Firmicutes* species, *Bacteroidetes* species, *Proteobacteria* species, *Verrumicrobia* species, *Actinobacteria* species, *Fusobacteria* species, *Cyanobacteria* species and the like. Archaea may include methanogens such as *Methanobrevibacter smithies*' and *Methanosphaera stadtmanae*. Fungi may include *Candida* species and *Malassezia* species. Viruses may include bacteriophages. Microbiome species may vary in different locations throughout the body. For example, the genitourinary system may contain a high prevalence of *Lactobacillus* species while the gastrointestinal tract may contain a high prevalence of *Bifidobacterium* species while the lung may contain a high prevalence of *Streptococcus* and *Staphylococcus* species.

With continued reference to FIG. 1, microbiome body measurement may include one or more stool test results describing presence, absence, and/or measurement of microorganisms including bacteria, archaea, fungi, protozoa, algae, viruses, parasites, worms, and the like. Stool test results may contain species such as Ackerman's muciniphila, *Anaerotruncus colihominis*, bacteriology, *Bacteroides* vulgates', *Bacteroides-Prevotella, Barnesiella* species, *Bifidobacterium* longarm, *Bifidobacterium* species, *Butyrivbrio crossotus, Clostridium* species, *Collinsella aerofaciens*, fecal color, fecal consistency, *Coprococcus eutactus, Desulfovibrio piger, Escherichia coli, Faecalibacterium prausnitzii*, Fecal occult blood, *Firmicutes* to *Bacteroidetes* ratio, *Fusobacterium* species, *Lactobacillus* species, *Methanobrevibacter smithii*, yeast minimum inhibitory concentration, bacteria minimum inhibitory concentration, yeast mycology, fungi mycology, *Odoribacter* species, Oxalobacter formigenes, parasitology, *Prevotella* species,

*Pseudoflavonifractor* species, *Roseburia* species, *Ruminococcus* species, *Veillonella* species and the like.

With continued reference to FIG. 1, microbiome body measurement may include one or more stool tests results that identify all microorganisms living a user's gut including bacteria, viruses, archaea, yeast, fungi, parasites, and bacteriophages. Microbiome body measurement may include DNA and RNA sequences from live microorganisms that may impact a user's health. Microbiome body measurement may include high resolution of both species and strains of all microorganisms. Microbiome body measurement may include data describing current microbe activity. Microbiome body measurement may include expression of levels of active microbial gene functions. Microbiome body measurement may include descriptions of sources of disease causing microorganisms, such as viruses found in the gastrointestinal tract such as raspberry bushy swarf virus from consuming contaminated raspberries or Pepino mosaic virus from consuming contaminated tomatoes.

With continued reference to FIG. 1, microbiome body measurement may include one or more blood test results that identify metabolites produced by microorganisms. Metabolites may include for example, indole-3-propionic acid, indole-3-lactic acid, indole-3-acetic acid, tryptophan, serotonin, kynurenine, total indoxyl sulfate, tyrosine, xanthine, 3-methylxanthine, uric acid, and the like.

With continued reference to FIG. 1, microbiome body measurement may include one or more breath test results that identify certain strains of microorganisms that may be present in certain areas of a user's body. This may include for example, lactose intolerance breath tests, methane-based breath tests, hydrogen based breath tests, fructose based breath tests. *Helicobacter pylori* breath test, fructose intolerance breath test, bacterial overgrowth syndrome breath tests and the like.

With continued reference to FIG. 1, microbiome body measurement may include one or more urinary analysis results for certain microbial strains present in urine. This may include for example, urinalysis that examines urine specific gravity, urine cytology, urine sodium, urine culture, urinary calcium, urinary hematuria, urinary glucose levels, urinary acidity, urinary protein, urinary nitrites, bilirubin, red blood cell urinalysis, and the like.

With continued reference to FIG. 1, nutrient as used herein, includes any substance required by the human body to function. Nutrients may include carbohydrates, protein, lipids, vitamins, minerals, antioxidants, fatty acids, amino acids, and the like. Nutrients may include for example vitamins such as thiamine, riboflavin, niacin, pantothenic acid, pyridoxine, biotin, folate, cobalamin, Vitamin C, Vitamin A, Vitamin D, Vitamin E, and Vitamin K. Nutrients may include for example minerals such as sodium, chloride, potassium, calcium, phosphorous, magnesium, sulfur, iron, zinc, iodine, selenium, copper, manganese, fluoride, chromium, molybdenum, nickel, aluminum, silicon, vanadium, arsenic, and boron.

With continued reference to FIG. 1, nutrients may include extracellular nutrients that are free floating in blood and exist outside of cells. Extracellular nutrients may be located in serum. Nutrients may include intracellular nutrients which may be absorbed by cells including white blood cells and red blood cells.

With continued reference to FIG. 1, nutrient body measurement may include one or more blood test results that identify extracellular and intracellular levels of nutrients. Nutrient body measurement may include blood test results that identify serum, white blood cell, and red blood cell levels of nutrients. For example, nutrient body measurement may include serum, white blood cell, and red blood cell levels of micronutrients such as Vitamin A, Vitamin B1, Vitamin B2, Vitamin B3, Vitamin B6, Vitamin B12, Vitamin B5, Vitamin C, Vitamin D, Vitamin E, Vitamin K1, Vitamin K2, and folate.

With continued reference to FIG. 1, nutrient body measurement may include one or more blood test results that identify serum, white blood cell and red blood cell levels of nutrients such as calcium, manganese, zinc, copper, chromium, iron, magnesium, copper to zinc ratio, choline, inositol, carnitine, methylmalonic acid (MMA), sodium, potassium, asparagine, glutamine, serine, coenzyme q10, cysteine, alpha lipoic acid, glutathione, selenium, eicosapentaenoic acid (EPA), docosahexaenoic acid (DHA), docosapentaenoic acid (DPA), total omega-3, lauric acid, arachidonic acid, oleic acid, total omega 6, and omega 3 index.

With continued reference to FIG. 1, nutrient body measurement may include one or more salivary test results that identify levels of nutrients including any of the nutrients as described herein. Nutrient body measurement may include hair analysis of levels of nutrients including any of the nutrients as described herein.

With continued reference to FIG. 1, genetic as used herein, includes any inherited trait. Inherited traits may include genetic material contained with DNA including for example, nucleotides. Nucleotides include adenine (A), cytosine (C), guanine (G), and thymine (T). Genetic information may be contained within the specific sequence of an individual's nucleotides and sequence throughout a gene or DNA chain. Genetics may include how a particular genetic sequence may contribute to a tendency to develop a certain disease such as cancer or Alzheimer's disease.

With continued reference to FIG. 1, genetic body measurement may include one or more results from one or more blood tests, hair tests, skin tests, urine, amniotic fluid, buccal swabs and/or tissue test to identify a user's particular sequence of nucleotides, genes, chromosomes, and/or proteins. Genetic body measurement may include tests that example genetic changes that may lead to genetic disorders. Genetic body measurement may detect genetic changes such as deletion of genetic material or pieces of chromosomes that may cause Duchenne Muscular Dystrophy. Genetic body measurement may detect genetic changes such as insertion of genetic material into DNA or a gene such as the BRCA1 gene that is associated with an increased risk of breast and ovarian cancer due to insertion of 2 extra nucleotides. Genetic body measurement may include a genetic change such as a genetic substitution from a piece of genetic material that replaces another as seen with sickle cell anemia where one nucleotide is substituted for another. Genetic body measurement may detect a genetic change such as a duplication when extra genetic material is duplicated one or more times within a person's genome such as with Charcot-Marie Tooth disease type 1. Genetic body measurement may include a genetic change such as an amplification when there is more than a normal number of copies of a gene in a cell such as HER2 amplification in cancer cells. Genetic body measurement may include a genetic change such as a chromosomal translocation when pieces of chromosomes break off and reattach to another chromosome such as with the BCR-ABL1 gene sequence that is formed when pieces of chromosome 9 and chromosome 22 break off and switch places. Genetic body measurement may include a genetic change such as an inversion when one chromosome experiences two breaks and the middle piece is flipped or inverted before reattaching. Genetic body measurement may include a repeat such as when regions of DNA contain a sequence of nucleotides that repeat a number of times such as for example in Huntington's disease or Fragile X syndrome. Genetic body measurement may include a genetic change such as a trisomy when there are three chromosomes instead of the usual pair as seen with Down syndrome with a trisomy of chromosome 21, Edwards syndrome with a trisomy at chromosome 18 or Patau syndrome with a trisomy at chromosome 13. Genetic body measurement may include a genetic change such as monosomy such as when there is an absence of a chromosome instead of a pair, such as in Turner syndrome.

With continued reference to FIG. 1, genetic body measurement may include an analysis of COMT gene that is responsible for producing enzymes that metabolize neurotransmitters. Genetic body measurement may include an analysis of DRD2 gene that produces dopamine receptors in the brain. Genetic body measurement may include an analysis of ADRA2B gene that produces receptors for noradrenaline. Genetic body measurement may include an analysis of 5-HTTLPR gene that produces receptors for serotonin. Genetic body measurement may include an analysis of BDNF gene that produces brain derived neurotrophic factor. Genetic body measurement may include an analysis of 9p21 gene that is associated with cardiovascular disease risk. Genetic body measurement may include an analysis of APOE gene that is involved in the transportation of blood lipids such as cholesterol. Genetic body measurement may include an analysis of NOS3 gene that is involved in producing enzymes involved in regulating vaso-dilation and vaso-constriction of blood vessels.

With continued reference to FIG. 1, genetic body measurement may include ACE gene that is involved in producing enzymes that regulate blood pressure. Genetic body measurement may include SLCO1B1 gene that directs pharmaceutical compounds such as statins into cells. Genetic body measurement may include FUT2 gene that produces enzymes that aid in absorption of Vitamin B12 from digestive tract. Genetic body measurement may include MTHFR gene that is responsible for producing enzymes that aid in metabolism and utilization of Vitamin B9 or folate. Genetic body measurement may include SHMT1 gene that aids in production and utilization of Vitamin B9 or folate. Genetic body measurement may include MTRR gene that produces enzymes that aid in metabolism and utilization of Vitamin B12. Genetic body measurement may include MTR gene that produces enzymes that aid in metabolism and utilization of Vitamin B12. Genetic body measurement may include FTO gene that aids in feelings of satiety or fullness after eating. Genetic body measurement may include MC4R gene that aids in producing hunger cues and hunger triggers. Genetic body measurement may include APOA2 gene that directs body to produce ApoA2 thereby affecting absorption of saturated fats. Genetic body measurement may include UCP1 gene that aids in controlling metabolic rate and thermoregulation of body. Genetic body measurement may include TCF7L2 gene that regulates insulin secretion. Genetic body measurement may include AMY1 gene that aids in digestion of starchy foods. Genetic body measurement may include MCM6 gene that controls production of lactase enzyme that aids in digesting lactose found in dairy products. Genetic body measurement may include BCMO1 gene that aids in producing enzymes that aid in metabolism and activation of Vitamin A. Genetic body measurement may include SLC23A1 gene that produce and transport Vitamin C. Genetic body measurement may include CYP2R1 gene that produce enzymes involved in production and activation of Vitamin D. Genetic body measurement may include GC gene that produce and transport Vitamin D. Genetic body measurement may include CYP1A2 gene that aid in metabolism and elimination of caffeine. Genetic body measurement may include CYP17A1 gene that produce enzymes that convert progesterone into androgens such as androstenedione, androstendiol, dehydroepiandrosterone, and testosterone.

With continued reference to FIG. 1, genetic body measurement may include CYP19A1 gene that produce enzymes that convert androgens such as androstenedione and testosterone into estrogens including estradiol and estrone. Genetic body measurement may include SRD5A2 gene that aids in production of enzymes that convert testosterone into dihydrotestosterone. Genetic body measurement may include UFT2B17 gene that produces enzymes that metabolize testosterone and dihydrotestosterone. Genetic body measurement may include CYP1A1 gene that produces enzymes that metabolize estrogens into 2 hydroxy-estrogen. Genetic body measurement may include CYP1B1 gene that produces enzymes that metabolize estrogens into 4 hydroxy-estrogen. Genetic body measurement may include CYP3A4 gene that produces enzymes that metabolize estrogen into 16 hydroxy-estrogen. Genetic body measurement may include COMT gene that produces enzymes that metabolize 2 hydroxy-estrogen and 4 hydroxy-estrogen into methoxy estrogen. Genetic body measurement may include GSTT1 gene that produces enzymes that eliminate toxic by-products generated from metabolism of estrogens. Genetic body measurement may include GSTM1 gene that produces enzymes responsible for eliminating harmful by-products generated from metabolism of estrogens. Genetic body measurement may include GSTP1 gene that produces enzymes that eliminate harmful by-products generated from metabolism of estrogens. Genetic body measurement may include SOD2 gene that produces enzymes that eliminate oxidant by-products generated from metabolism of estrogens.

With continued reference to FIG. 1, metabolic, as used herein, includes any process that converts food and nutrition into energy. Metabolic may include biochemical processes that occur within the body. Metabolic body measurement may include blood tests, hair tests, skin tests, amniotic fluid, buccal swabs and/or tissue test to identify a user's metabolism. Metabolic body measurement may include blood tests that examine glucose levels, electrolytes, fluid balance, kidney function, and liver function. Metabolic body measurement may include blood tests that examine calcium levels, albumin, total protein, chloride levels, sodium levels, potassium levels, carbon dioxide levels, bicarbonate levels, blood urea nitrogen, creatinine, alkaline phosphatase, alanine amino transferase, aspartate amino transferase, bilirubin, and the like.

With continued reference to FIG. 1, metabolic body measurement may include one or more blood, saliva, hair, urine, skin, and/or buccal swabs that examine levels of hormones within the body such as 11-hydroxy-androstereone, 11-hydroxy-etiocholanolone, 11-keto-androsterone, 11-keto-etiocholanolone, 16 alpha-hydroxyestrone, 2-hydroxyestrone, 4-hydroxyestrone, 4-methoxyestrone, androstanediol, androsterone, creatinine, DHEA, estradiol, estriol, estrone, etiocholanolone, pregnanediol, pregnanestriol, specific gravity, testosterone, tetrahydrocortisol, tetrahydrocrotisone, tetrahydrodeoxycortisol, allo-tetrahydrocortisol.

With continued reference to FIG. 1, metabolic body measurement may include one or more metabolic rate test results such as breath tests that may analyze a user's resting metabolic rate or number of calories that a user's body burns each day rest. Metabolic body measurement may include one or more vital signs including blood pressure, breathing rate, pulse rate, temperature, and the like. Metabolic body measurement may include blood tests such as a lipid panel such as low density lipoprotein (LDL), high density lipoprotein (HDL), triglycerides, total cholesterol, ratios of lipid levels such as total cholesterol to HDL ratio, insulin sensitivity test, fasting glucose test, Hemoglobin A1C test, adipokines such as leptin and adiponectin, neuropeptides such as ghrelin, pro-inflammatory cytokines such as interleukin 6 or tumor necrosis factor alpha, anti-inflammatory cytokines such as interleukin 10, markers of antioxidant status such as oxidized low-density lipoprotein, uric acid, paraoxonase 1. Persons skilled in the art, upon reviewing the entirety of this disclosure, will be aware of various additional examples of physiological state data that may be used consistently with descriptions of systems and methods as provided in this disclosure.

With continued reference to FIG. 1, physiological data may be obtained from a physically extracted sample. A "physical sample" as used in this example, may include any sample obtained from a human body of a user. A physical sample may be obtained from a bodily fluid and/or tissue analysis such as a blood sample, tissue, sample, buccal swab, mucous sample, stool sample, hair sample, fingernail sample and the like. A physical sample may be obtained from a device in contact with a human body of a user such as a microchip embedded in a user's skin, a sensor in contact with a user's skin, a sensor located on a user's tooth, and the like. Physiological data may be obtained from a physically extracted sample. A physical sample may include a signal from a sensor configured to detect physiological data of a user and record physiological data as a function of the signal. A sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MM) equipment, ultrasound equipment, optical scanning equipment such as photo-plethysmographic equipment, or the like. A sensor may include any electromagnetic sensor, including without limitation electroencephalographic sensors, magnetoencephalographic sensors, electrocardiographic sensors, electromyographic sensors, or the like. A sensor may include a temperature sensor. A sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. A sensor may detect any hematological parameter including blood oxygen level, pulse rate, heart rate, pulse rhythm, blood sugar, and/or blood pressure. A sensor may be configured to detect internal and/or external biomarkers and/or readings. A sensor may be a part of system 100 or may be a separate device in communication with system 100.

With continued reference to FIG. 1, system 100 may include a remote device 116. Remote device 116 may include without limitation, a display in communication with computing device 104, where a display may include any display as described herein. Remote device 116 may include an additional computing device, such as a mobile device, laptop, desktop, computer and the like. Remote device 116 may transmit and/or receive one or more inputs from computing device 104 utilizing any network methodology as described herein. Remote device 116 may be operated by a user which may include any human subject. Remote device 116 may be operated by an informed advisor. An "informed advisor" as used in this disclosure may include any health professional who may be responsible for organizing and/or delivering healthcare to a user. An informed advisor may include for example a functional medicine doctor, a yoga teacher, a reiki instructor, a psychologist, a nurse, a pharmacist, a dentist, a physician assistant, a nurse practitioner, a spiritual coach, a life coach, a health coach, a psychiatrist, a psychologist, and the like. Remote device 116 may transmit to computing device 104 one or more biological extractions to be stored in biological database 108. For instance and without limitation, remote device 116 may include a mobile phone operated by a user which may be utilized by the user to transmit blood test results that a user had analyzed at a recent appointment with the user's functional medicine physician. In yet another non-limiting example, remote device 116 may include a sensor that may track a user's heart rate during a yoga class which user may then transmit to computing device 104 to be stored in biological database 108. In yet another non-limiting example, remote device 116 may include a tablet operated by an informed advisor such as user's spiritual coach who may transmit one or more biological extractions obtained during a recent session between the user and the user's spiritual coach which may then be stored in biological database 108.

With continued reference to FIG. 1, system 100 may include a biological capture device 120. A "biological capture device 120" as used in this disclosure, includes any device that may be utilized to obtain a biological extraction. A device utilized to obtain a biological extraction may include a sensor, a fingerpick device utilized to obtain a blood sample, an imaging device such as a computed tomography (CT) machine, a magnetic resonance imaging (MM) machine, a needle, a collection tube utilized to collect a fluid or tissue sample such as a salivary sample or a stool sample, an optical image machine such as a camera or scanner and the like. Biological capture device 120 may include any device suitable for use as remote device 116. In an embodiment, biological capture device 120 may be contained within remote device 116.

With continued reference to FIG. 1, user activity profile 112 includes at least an element of user activity data. "User activity data" as used in this disclosure, includes any data describing any particular activity the user may have been engaged in either before, during, or after collection of a biological extraction. "Activity" as used in this disclosure, includes any action that requires physical effort which may be performed to sustain or improve one's health. Activity may include movement that a user may engage upon such as walking around user's house, shoveling snow on user's driveway, performing movement at a gym such as by exercising on a machine such as a treadmill or Stairmaster, participating in a group exercise class, performing a meditation sequence, practicing a yoga sequence, lifting weights, performing one or more exercise routines, strolling down a street to breathe in fresh air, performing a series of twists or stretches, and the like. Activity may include subconscious movement such as one's body movements while sleeping that include rolling from side to side while sleeping. Activity may include one or more exertions such as folding laundry, performing housework, cleaning dishes, dusting, carrying groceries, and the like. User activity data may include a description of one or more activities that a user engages in either before, during, or after collection of a particular biological extraction. For instance and without limitation, user activity data may indicate that a biological extraction such as a fasting blood glucose level was obtained after a user swam three miles. In yet another non-limiting example, user activity data may include that a biological extraction such as user's heart rate that was monitored while user participated in a spinning class. In yet another non-limiting example, user activity data may include a description of a yoga sequence user practiced after providing a stool sample.

With continued reference to FIG. 1, computing device 104 is configured to generate using fitness training data 124 wherein fitness training data 124 includes a plurality of activity profiles and a plurality of correlated fitness profiles, and using a classification algorithm, a fitness classifier, wherein the fitness classifier inputs activity profiles and outputs fitness profiles. Training data, as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

With continued reference to FIG. 1, "fitness training data 124" as used in this disclosure, includes training data that includes a plurality of data entries each data entry containing activity profiles and correlated fitness profiles. Fitness training data 124 and/or elements thereof may be entered by one or more users including for example, by one or more experts from remote device 116. Experts may include one or more physicians, fitness trainers, experts in exercise and the like who may contain one or more credentials that may certify them as an expert. Credentials may include one or more licenses such as a medical license or a certified fitness coach license. Credentials may include one or more board certifications such as a certified personal trainer, a certified group exercise instructor, a certified exercise physiologist, a certified medical exercise specialist, a certification from an organization relating to exercise such as the American College of Sports Medicine and the like. Credentials may include a particular field of experience and practice such as a sports medicine doctor, orthopedic doctor, physiatrist, and the like. Credentials may include publications in top leading medical journals, newspapers, and articles. Credentials may include participation in one or more clinical trials.

With continued reference to FIG. 1, system 100 may include a graphical user interface 128. Graphical user interface 128 may include without limitation a form or other graphical element having data entry fields, wherein a user such as an expert may select one or more fields to enter one or more training sets. Graphical user interface 128 may provide a drop-down menu where an expert may select a particular topic or category to enter a particular training set in relationship to. For instance and without limitation, an expert may have significant experience relating to particular forms of cardiovascular exercises best suited for individuals with high fasting blood glucose levels. In such an instance, expert may select a category displayed in a drop-down menu on graphical user interface 128 to select an entry relating to biological extractions that include glucose levels. Graphical user interface 128 may provide free form textual entry fields where an expert may enter one or more topics or categories that are of particular interest to an expert or that an expert has significant experience in treating and/or mitigating. Graphical user interface 128 may also be utilized to display one or more outputs to a user such particular recommended exercise as described in more detail below.

With continued reference to FIG. 1, fitness training data 124 includes a plurality of activity profiles and a plurality of correlated fitness profiles. A "fitness profile" as used in this disclosure, includes an expected level of fitness for a user that a user should be able to perform or achieve based on certain criteria such as input by experts and fitness professionals. A preferred fitness level includes a description of one or more physical activities that an average user classified to a particular fitness profile should be able to perform. A preferred fitness level may include a description of one or more target ranges, reference ranges, usual responses, and/or findings that a biological extraction should fall within for a user at this particular preferred fitness level. A fitness profile may include a selection of one or more training sets that may be relevant for a user who may be classified to this particular fitness profile. Relevant training sets pertaining to one or more fitness profiles may be stored within training database 132. Training database 132 may include any data structure suitable for use as biological database 108 as described above.

With continued reference to FIG. 1, computing device 104 may generate fitness classifier 136 using a classification algorithm 140, defined as a process whereby a computing device 104 derives, from training data, a model known as a "classifier" for sorting inputs into categories or bins of data. Fitness classifier 136 includes any classifier as described herein. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate fitness classifier 136 using a Naïve Bayes classification algorithm 140. Naïve Bayes classification algorithm 140 generates classifiers by assigning class labels to problem instances, represented as vectors of element values. Class labels are drawn from a finite set. Naïve Bayes classification algorithm 140 may include generating a family of algorithms that assume that the value of a particular element is independent of the value of any other element, given a class variable. Naïve Bayes classification algorithm 140 may be based on Bayes Theorem expressed as P(A/B)=P(B/A) P(A)÷P(B), where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm 140 may include a gaussian model that follows a normal distribution. Naïve Bayes classification algorithm 140 may include a multinomial model that is used for discrete counts. Naïve Bayes classification algorithm 140 may include a Bernoulli model that may be utilized when vectors are binary.

With continued reference to FIG. 1, computing device 104 may be configured to generate fitness classifier 136 using a K-nearest neighbors (KNN) algorithm. A "K-nearest neighbors algorithm" as used in this disclosure, includes a classification method that utilizes feature similarity to analyze how closely out-of-sample—features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm $$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting example, K-nearest neighbors algorithm may be configured to classify an input vector including a user activity profile 112, to clusters representing fitness profiles.

With continued reference to FIG. 1, generating fitness classifier 136 by computing device 104 may include extracting from a user activity profile 112 an activity descriptor relating to a biological extraction and inputting the biological extraction and the activity descriptor relating to the biological extraction into the fitness classifier 136. An "activity descriptor" as used in this disclosure, includes a description of one or more activities that a user has engaged in. An activity descriptor may include a description of any activity that a user may practice, participate in, and/or engage in. Activity descriptor may include any activity that may not necessarily have been practiced or performed immediately before, during, or after a biological extraction. For example, an activity descriptor may include a description of a rock climbing class user participates in three days each week, but which user was not participating in when user's blood was drawn to check user's hemoglobin levels. For instance and without limitation, computing device 104 may extract from a user activity profile 112 an activity descriptor such as a descriptor of a spinning class that user was engaged in while user's temperature was measured. In such an instance, the spinning class that the user participated in while user obtained temperature readings may be input by computing device 104 into the fitness classifier 136 to generate an output that includes a fitness profile. Generating fitness classifier 136 may include retrieving by the computing device 104 a plurality of chronological user biological extractions from biological database 108. "Chronological biological extractions" as used in this disclosure, includes a series of two or more user biological extractions obtained at two or more different points in time. Chronological biological extractions may include two or more measurements of the same biological extraction and/or two or more measurements of two or more different biological extractions. Chronologically obtained biological extractions may include biological extractions obtained at two different points in time which may include two or more biological extractions obtained immediately after one another, or after the passage of a certain interval of time such as a nanosecond, millisecond, second, minute, hour, day, week, month, year and the like. Computing device 104 classifies a plurality of chronological user biological extractions to each contain a classification label. A "classification label" as used in this disclosure, includes a label that indicates whether an input belongs to a particular class or not. A class may include any output generated by a classification algorithm 140. Classification algorithm 140 may include any of the classification algorithm 140 as described herein. Computing device 104 may generate classification labels that may indicate whether a particular biological extraction is within normal limits or not within normal limits. "Normal limits" as used in this disclosure, include a set of upper and lower limits given a range value for a particular biological extraction. Normal limits may include a classification label that indicates whether a particular biological extraction contains normal or abnormal findings such as when a biological extraction may include a particular imaging scan such as an MRI or CT scan. Normal limits may be generated based on expert input, including any of the expert input as described above. Normal limits may be generated based on factors that include sex, age, race, medical history, general health and the like. Normal limits may be generated based on one or more third parties that may analyzed a particular biological extraction such as a particular laboratory that may analyze a urine sample may have certain established normal limits while a particular laboratory that may analyze a blood sample may have certain established normal limits. Chronological biological extractions that contain a classification label may indicating if a biological extraction is within normal limits or not within normal limits may then be input into fitness classifier 136.

With continued reference to FIG. 1, computing device 104 calculates using the fitness classifier 136 and a classification algorithm 140 an output that includes a selected fitness profile 144 utilizing the fitness training data 124. A "selected fitness profile 144" as used in this disclosure, is a fitness profile, as defined above, that is selected by fitness classifier 136 as a result of calculating a classification algorithm 140. Selected fitness profile 144 includes a particular fitness profile selected from a plurality of fitness profiles. Selected fitness profile 144 may include any of the fitness profiles as described above.

With continued reference to FIG. 1, computing device 104 is configured to classify using the fitness classifier 136 a classification algorithm 140 utilizing the user activity profile 112 as an input and output a fitness profile utilizing the fitness training data 124. Computing device 104 may generate a classification algorithm 140 that includes any of the classification algorithm 140 as described above. Fitness profile includes any of the fitness profiles as described above.

With continued reference to FIG. 1, computing device 104 is configured to select using a selected fitness profile an activity training set 148. Activity training set 148 is a training set that includes plurality of fitness profiles and a plurality of correlated fitness recommendations. "Fitness recommendations" as used in this disclosure, includes one or more suggested exercises that a user may consider partaking in. Exercises may include any of the activities as described above. Fitness recommendations may include different groups of exercises such as cardiovascular activities, strength and toning activities, meditative activities, relaxing activities and the like. Fitness recommendations may include specific implementation details that contain information describing how long a user should practice a particular exercise, how intense a user should practice a particular exercise at, how often a user should practice a particular exercise, how a particular exercise can be modified to different intensity levels and the like. For example, fitness recommendations may include a suggestion that include swimming three miles two days each week and practicing yoga three days each week for thirty minutes at a moderate intensity. In yet another non-limiting example, fitness recommendations may include a recommendation that include engaging in all cardiovascular activities for a total of 150 minutes but stopping if user's heart rate rises above 200 beats per minute.

With continued reference to FIG. 1, computing device 104 may select an activity training set 148 from training database 132. Activity training set 148 may be selected by classifying a fitness profile to contain an activity classification label containing an activity level. An activity classification label may include any classification label as described above. Activity classification label may be generated using any of the classification labels as described above. Activity classification label may indicate an activity level of a particular fitness profile. Activity level may indicate if a fitness profile indicates a beginner activity level, such as a user who may be new to practicing any level of fitness. Activity level may indicate an intermediate activity level such as a user who may routinely engage in activity but who is not an expert and who may still be capable of achieving higher levels of fitness or who may be able to engage in more and/or greater fitness levels. Activity level may include an accelerated activity level such as a user who habitually engages in activity. Activity levels may also indicate particular types of activities that a particular fitness profile engages in. For example, activity level may indicate cardiovascular activities, stretching activities, running activities, sprinting activities, marathon activities, weightlifting activities and the like. One or more activity classification labels may be generated based on expert input, including any of the expert input as described above. Computing device 104 may select an activity training set 148 as a function of an activity classification label. In an embodiment, activity training set 148 may be organized and stored within training database 132 according to activity level. Computing device 104 may select an activity training set 148 that matches an activity classification label.

With continued reference to FIG. 1, computing device 104 generates using an activity training set 148 and a selected fitness profile a feature learning model utilizing a feature learning algorithm 152. Feature learning algorithm 152 inputs fitness profiles and outputs recommended exercise. A "feature learning model" as used herein, includes any machine-learning model as described herein. A feature learning model may include performing a series of one or more calculations, algorithms, and/or equations. A feature learning model may be generated using one or more feature learning algorithms. A "feature learning algorithm 152," as used herein, is a machine-learning algorithm that identifies associations between elements of data in a training data set, where particular outputs and/or inputs are not specified. For instance, and without limitation, a feature learning algorithm 152 may detect co-occurrences of sets of fitness profiles, as defined above, with each other and with recommended exercise. As a non-limiting example, feature learning algorithm 152 may detect co-occurrences of fitness profiles, as defined above, with each other and with cardiovascular exercise. Feature learning algorithm 152 may include supervised feature learning algorithms that may be learned using labeled training data. For example, supervised feature learning algorithm 152 may include supervised neural networks, multilayer perceptron, and/or supervised dictionary learning. Feature learning algorithm 152 may include unsupervised machine learning algorithms that may be learned using unlabeled training data. Unsupervised feature learning algorithm 152 may include k-means clustering, principal component analysis, local linear embedding, intendent component analysis, unsupervised dictionary learning, restricted Boltzmann machine, and/or autoencoder. Computing device 104 may perform a feature learning algorithm 152 by dividing fitness profiles into various sub-combinations of such data to create fitness profile data sets, and evaluate which fitness datasets tend to co-occur with other fitness profile data sets, and recommended exercise; for instance, where fitness profile data includes cardiovascular exercise, computing device 104 may divide each exercise into individual data sets to identify which individual exercises and/or combinations thereof tend to co-occur with which other individual exercises, fitness profiles, and/or recommended exercise. In an embodiment, feature learning algorithm 152 may perform clustering of data; for instance, a number of clusters into which data from training data sets may be sorted using feature learning may be set as a number of recommended exercises.

Continuing refer to FIG. 1, a feature learning and/or clustering algorithm may be implemented, as a non-limiting example, using a k-means clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean, using, for instance behavioral training set 124 as described above. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster; for instance, and without limitation, a fuzzy clustering algorithm may be used to identify clustering of gene combinations with multiple disease states, and vice versa. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, computing device 104 may generate a k-means clustering algorithm receiving unclassified fitness profile data and/or combinations thereof as inputs and outputs a definite number of classified data entry cluster wherein the data entry clusters each contain cluster data entries each containing recommended exercise. K-means algorithm may select a specific number of groups or clusters to output, identified by a variable "k." Generating a k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm may act to classify a given fitness profile to one or more recommended exercise, enabling computing device 104 to identify.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids $c_i$ of centroids in set C. Unclassified data may be assigned to a cluster based on $\text{argmin}_{ci} \ni_c \text{dist}(ci, x)^2$, where argmin includes argument of the minimum, ci includes a collection of centroids in a set C, and dist includes standard Euclidean distance. K-means clustering module may then recompute centroids by taking mean of all cluster data entries assigned to a centroid's cluster. This may be calculated based on $ci=1/|Si|\Sigma xi \ni Si^{xi}$. K-means clustering algorithm may continue to repeat these calculations until a stopping criterion has been satisfied such as when cluster data entries do not change clusters, the sum of the distances have been minimized, and/or some maximum number of iterations has been reached.

Still referring to FIG. 1, k-means clustering algorithm may be configured to calculate a degree of similarity index value. A "degree of similarity index value" as used in this disclosure, includes a distance measurement indicating a measurement between each data entry cluster generated by k-means clustering algorithm and a selected physiological data set and/or combination of genes, negative behaviors and/or negative behavioral propensities. Degree of similarity index value may indicate how close a particular fitness profile and/or recommended exercise is to being classified by k-means algorithm to a particular cluster. K-means clustering algorithm may evaluate the distances of the fitness profile and/or recommended exercise is to the k-number of clusters output by k-means clustering algorithm. Short distances between a fitness profile and/or recommended exercise and a cluster may indicate a higher degree of similarity between a fitness profile and/or recommended exercise and a particular cluster. Longer distances between a fitness profile and/or recommended exercise and a cluster may indicate a lower degree of similarity between a fitness profile and/or recommended exercise and a particular cluster.

With continued reference to FIG. 1, k-means clustering algorithm selects a classified data entry cluster as a function of the degree of similarity index value. In an embodiment, k-means clustering algorithm may select a classified data entry cluster with the smallest degree of similarity index value indicating a high degree of similarity between a fitness profile and/or recommended exercise and a particular data entry cluster. Alternatively or additionally k-means clustering algorithm may select a plurality of clusters having low degree of similarity index values to a fitness profile and/or recommended exercise, indicative of greater degrees of similarity. Degree of similarity index values may be compared to a threshold number indicating a minimal degree of relatedness suitable for inclusion of a fitness profile and/or recommended exercise in a cluster, where degree of similarity indices falling under the threshold number may be included as indicative of high degrees of relatedness. The above-described illustration of feature learning using k-means clustering is included for illustrative purposes only, and should not be construed as limiting potential implementation of feature learning algorithm 152; persons skilled in the art, upon reviewing the entirety of this disclosure, will be aware of various additional or alternative feature learning approaches that may be used consistently with this disclosure.

With continued reference to FIG. 1, computing device 104 identifies recommended exercise 156 for a user utilizing a user activity profile 112. "Recommended exercise" as used in this disclosure, includes any recommended exercise output by computing device 105 generated using activity training set and a selected fitness profile utilizing a feature learning algorithm. Recommended exercise may include one or more fitness suggestions for a user. Fitness suggestions may include particular exercises that a user should engage in, lengths of duration of particular exercises, intensity of exercises, frequency of exercise, and the like. Exercise may include the ability to practice and/or perform one or more sports, occupations, daily activities, mindfulness practices, breathing practices, relaxation practices, and the like. For example, exercise may include a particular form of exercise such as cardiovascular exercise. Exercise may include a specific exercise such as running on a treadmill, climbing on a Stairmaster, practicing hatha yoga, walking in nature and the like. Computing device 104 may identify exercises contained within a user activity profile 112. For example, a user activity profile 112 may indicate that a user participates in a spinning class, enjoys rock climbing or swims two miles every day. Computing device 104 compares recommended exercise generated by feature learning algorithm 152 to exercises contained within a user activity profile 112. Recommended exercise generated from feature learning algorithm 152 may impose one or more limitations or restrictions on a particular exercise. For example, recommended exercise generated from feature learning algorithm 152 may recommend that user can engage in cardiovascular exercises that include running, jogging, and biking but user cannot engage in spinning class because user's heart rate has been too elevated every time user has engaged in spinning and one or more of user's biological extractions indicate one or more genetic markers of heart disease. In yet another non-limiting example, recommended exercise may include one or more user specific modifications that indicate how user should modify a particular exercise or practice to best accommodate a user's needs and personal health. User specific modifications may allow a user to participate in a particular exercise but with modifications created based on one or more biological extractions and user health datums. For example, a user specific modification may indicate that a user should only engage in muscle strengthening exercise three days each week. In yet another non-limiting example, a user specific modification may indicate that a user can engage in yina yoga, vinyasa yoga, and hatha yoga but that the user must modify handstand pose and instead perform child's pose because user has carpel tunnel syndrome and a handstand pose would place excess stress on user's joints. In yet another non-limiting example, a user specific modification may include a suggestion that a user should engage in one or more recommended exercise only after eating because user's biological extractions indicate low fasting blood glucose levels upon waking. Recommended exercise may also include identifying non-recommended exercise that the user should not engage in. Non-recommended exercise may include any exercise that the user should not engage in. For instance and without limitation, recommended exercise may indicate that a user can engage in weightlifting, pushups, and kettle bell exercises but that a user cannot engage in a leg press due to a recently torn calf muscle. In yet another non-limiting example, recommended exercise may indicate that a user can engage in brisk walking, tennis matches, and playing golf but that the user cannot engage in swimming due to recent surgery on user's shoulder joint. Computing device compares recommended exercise to exercises contained within a user activity profile 112. Comparing may include determining if any of the activities match and if any of the activities contain one or more user specific modifications or non-recommended exercise. Computing device generates a recommended exercise instruction set. A "recommended exercise instruction set" as used in this disclosure, includes one or more suggested exercises suggested for a user to engage in and uniquely generated to account for one or more user biological extractions. Recommended exercise instruction set may be generated utilizing any of the methodologies as described above. Recommended exercise instruction set may be transmitted to a remote device 116. Remote device 116 may include any of the remote device 116 as described above. In an embodiment, remote device 116 may include a mobile phone operated by a user or a computer or tablet operated by one of user's informed advisors such as user's fitness coach or health coach. Alternatively or additionally, recommended exercise instruction set may be displayed on graphical user interface 128 located on computing device.

Figure 2:
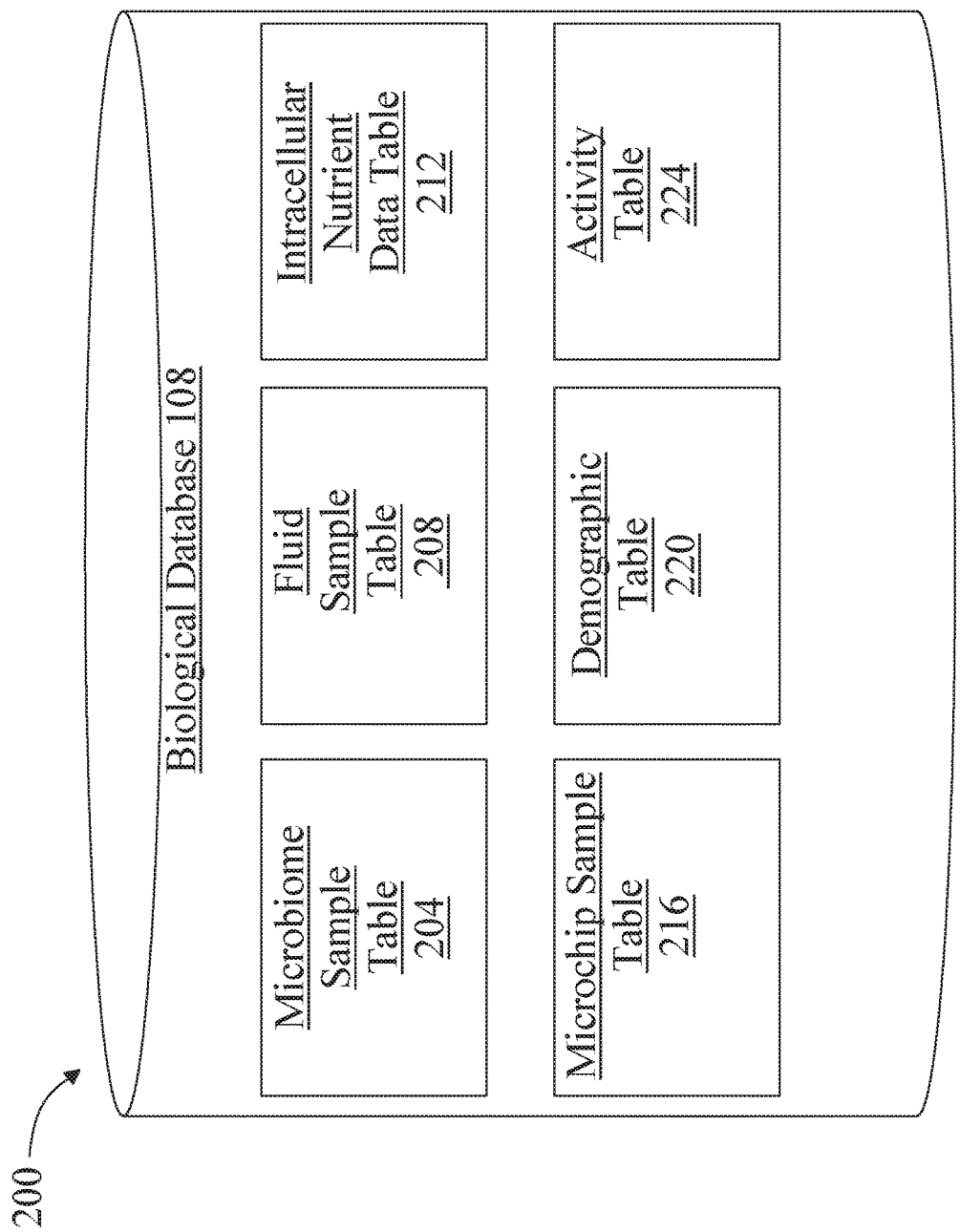
FIG. 2 is a block diagram illustrating an exemplary embodiment of a biological database.

Referring now to FIG. 2, an exemplary embodiment of biological database 108 is illustrated. Biological database 108 may be implemented as any data structure as described above. One or more tables contained within biological database 108 may include microbiome sample table 204; microbiome sample table 204 may include one or more biological extractions relating to the microbiome. For instance and without limitation, microbiome sample table 204 may include a physically extracted sample such as a stool sample analyzed for the presence of pathogenic species such as parasites and anaerobes. One or more tables contained within biological database 108 may include fluid sample table 208; fluid sample table 208 may include one or more biological extractions containing fluid samples. For instance and without limitation, fluid sample table 208 may include a urine sample analyzed for the presence or absence of glucose. One or more tables contained within biological database 108 may include intracellular nutrient data table 212; intracellular nutrient data table 212 may include one or more biological extractions containing intracellular nutrient levels. For instance and without limitation, intracellular nutrient data table 212 may include a blood sample analyzed for intracellular levels of Vitamin B12. One or more tables contained within biological database 108 may include microchip sample table 216; microchip sample table 216 may include one or more biological extractions obtained from a microchip. For instance and without limitation, microchip sample table 216 may include a blood sugar level obtained from a microchip embedded under a user's skin. One or more tables contained within biological database 108 may include demographic table 220; demographic table 220 may include one or more demographic inputs pertaining to a user. For instance and without limitation, demographic table 220 may include information pertaining to a user's full name, address, date of birth, sex, marital status, occupation, and the like. One or more tables contained within biological database 108 may include activity table 224; activity table 224 may include one or more elements of user activity data. For instance and without limitation, activity table 224 may include a description of one or more exercises that a user participates in, and/or one or more elements of user activity data.

Figure 3:
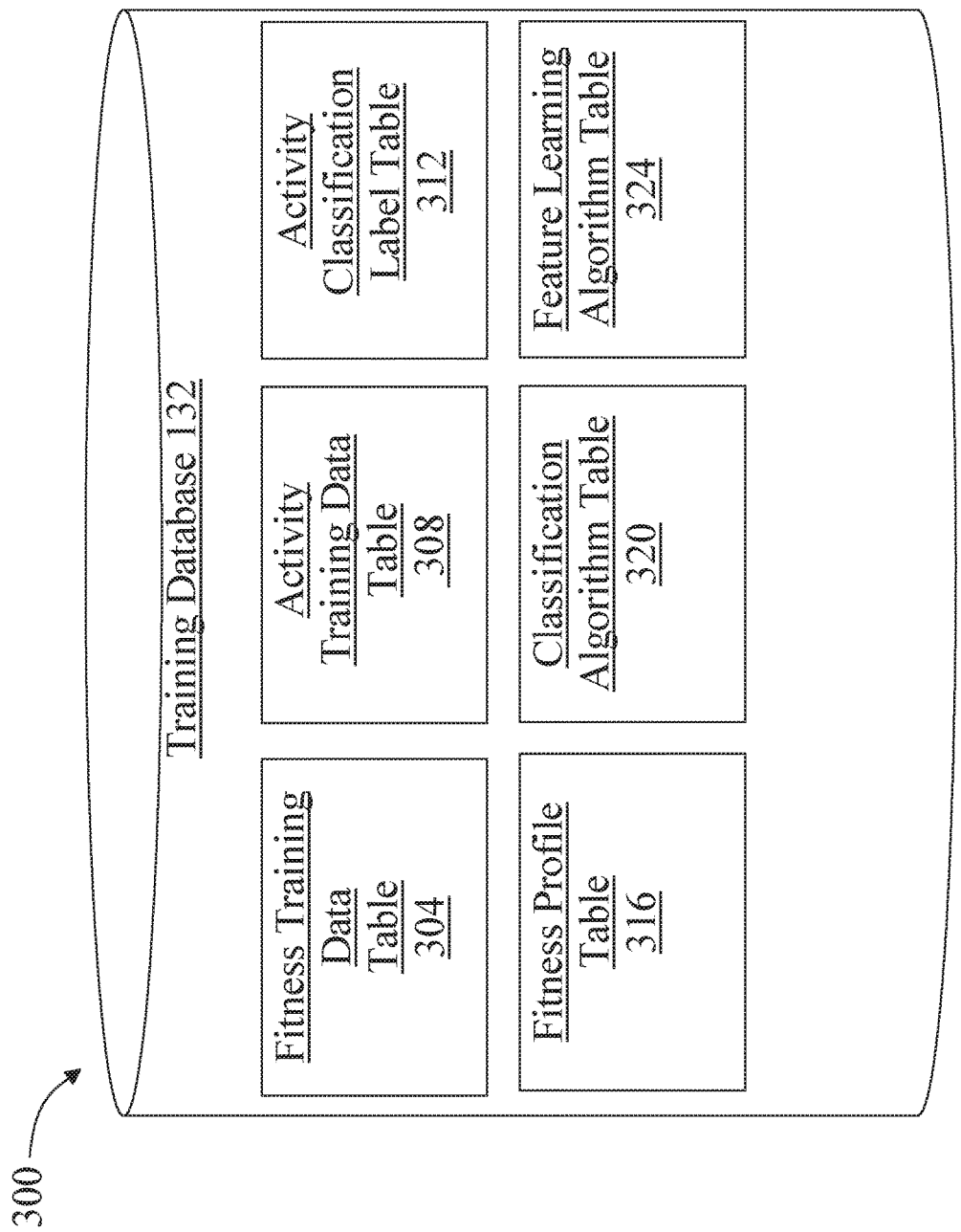
FIG. 3 is a block diagram illustrating an exemplary embodiment of a training database.

Referring now to FIG. 3, an exemplary embodiment of training database 132 is illustrated. Training database 132 may be implemented as any data structure suitable for use as biological database 108 as described above in more detail in FIG. 1. One or more tables contained within training database 132 may include fitness training data table 304; fitness training data table 304 may include one or more fitness training data 124 sets. One or more tables contained within training database 132 may include activity training data table 308; activity training data table 308 may include one or more activity training data sets. One or more tables contained within training database 132 may include activity classification label table 312; activity classification label table 312 may include one or more activity training data sets containing activity classification labels and/or stored in training database 132 by activity classification label. One or more tables contained within training database 132 may include fitness profile table 316; fitness profile table 316 may include one or more fitness profiles and/or one or more suggested training sets to be selected and utilized for one or more fitness profiles. One or more tables contained within training database 132 may include classification algorithm table 320; classification algorithm table 320 may include one or more classification algorithm 140. In an embodiment, one or more classification algorithm 140 contained within classification algorithm table 320 may be previously calculated and loaded into training database 132 thereby being able to be utilized to generate an output by computing device 104 more rapidly. One or more tables contained within training database 132 may include feature learning algorithm table 324; feature learning algorithm table 324 may include one or more feature learning algorithm 152. In an embodiment, one or more feature learning algorithm 152 contained within feature learning algorithm table 324 may be previously calculated and loaded into training database 132 thereby being able to be utilized to generate an output by computing device 104 more rapidly.

Figure 4:
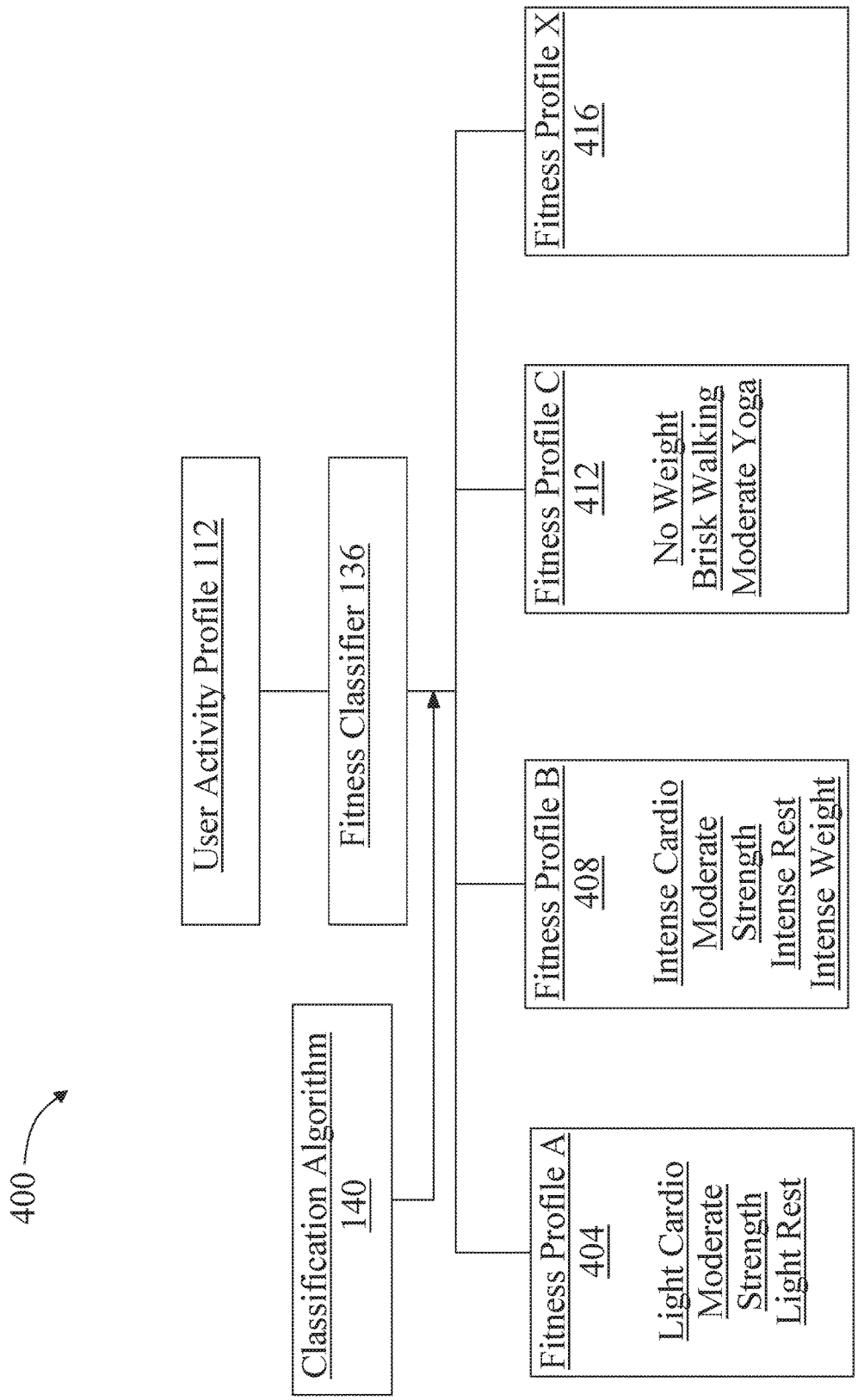
FIG. 4 is a diagrammatic representation of a fitness classifier.

Referring now to FIG. 4, an exemplary embodiment of fitness classifier 136 is illustrated. Fitness classifier 136 may be generated by computing device 104 utilizing any of the methodologies as described above. Fitness classifier 136 receives user activity profile 112 from biological database 108 as described above. User activity profile 112 includes a biological extraction and at least an element of user activity data. Fitness classifier 136 classifies using a classification algorithm 140 a user activity profile 112 as an input and outputs a fitness profile. Classification algorithm 140 includes any of the classification algorithm 140 as described above. Fitness profile includes any of the fitness profiles as described above. Fitness profile includes a preferred fitness level. Fitness classifier 136 may take into account additional factors beyond user activity profile 112 when using a classification algorithm 140 to output a fitness profile. Fitness classifier 136 may output a fitness profile by evaluating a user's age, sex, demographic information, and/or any other information that may be relevant pertaining to what exercises and/or routines that a user may or may not be able to perform. For example, fitness classifier 136 may not output a fitness profile that contains any exercises that utilize upper body strength and arm movement if a user has a broken shoulder. In yet another non-limiting example, fitness classifier 136 may not output a fitness profile that contains intense cardiovascular exercise for a user who recently suffered a heart attack. Fitness classifier 136 may take into account additional factors when necessary based on expert input. Expert input includes any of the expert input as described above.

With continued reference to FIG. 4, fitness classifier 136 selects a fitness profile. In an embodiment, fitness profile A 404 may include a description of one or more exercises contained within the fitness profile A such as light cardio, moderate strength, and light rest. In an embodiment, fitness profile B 408 may include intense cardio, moderate strength, intense rest, and intense weight. In an embodiment, fitness profile C 412 may include no weights, brisk walking, and moderate yoga. Classification algorithm 140 may aid fitness classifier 136 in selecting a fitness profile from fitness profile X 416 or an indefinite number of fitness profiles. Selection of a particular classification algorithm 140 that fitness classifier 136 may utilize to select a particular fitness profile may be contained within training database 132 as described above and may be based on expert input.

Figure 5:
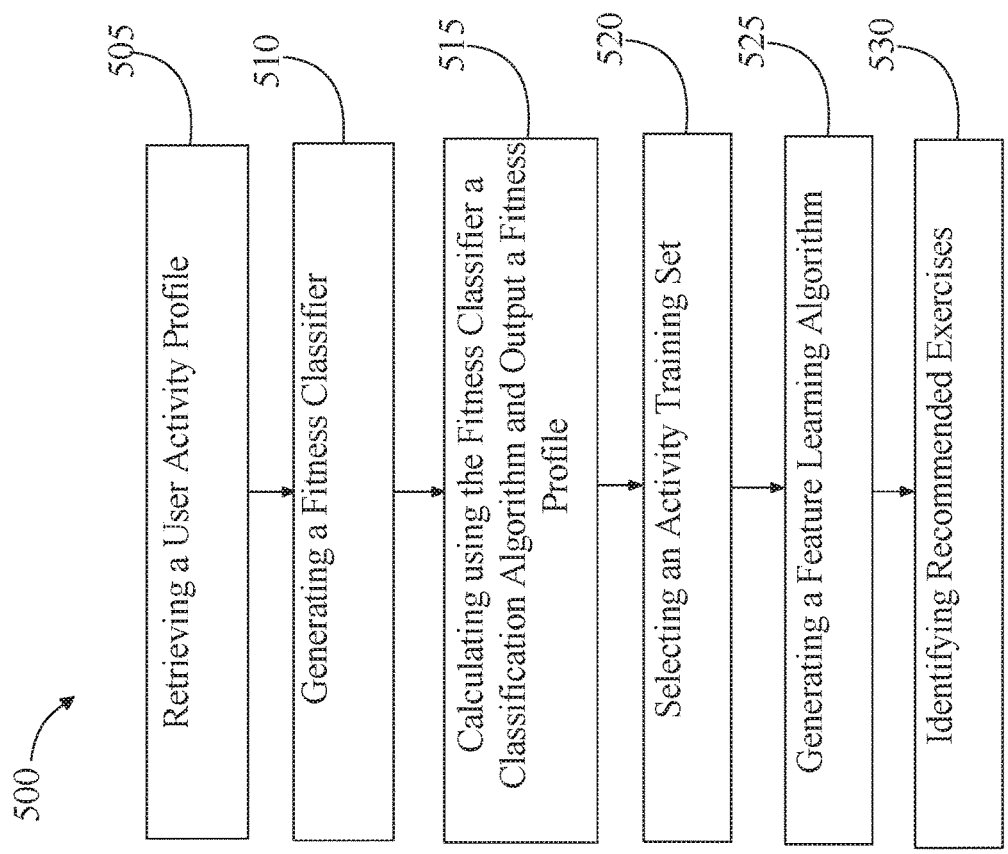
FIG. 5 is a process flow diagram illustrating an exemplary embodiment of a method of generating fitness recommendations according to user activity profiles.

Referring now to FIG. 5, an exemplary embodiment of a method 500 of generating fitness recommendations according to user activity profile 112 is illustrated. At step 505 a computing device retrieves from a biological database 108 a user activity profile 112 wherein the user activity profile 112 further comprises a biological extraction and at least an element of user activity data wherein the biological extraction further comprises at least an element of user physiological data. Biological extraction includes any of the biological extractions as described above in reference to FIG. 1. For instance and without limitation, a biological extraction may include one or more blood oxygenation levels obtained from a sensor worn on user's skin. In yet another non-limiting example, a biological extraction may include a stool sample analyzed for the presence or absence of particular bacteria. In yet another non-limiting example, a biological extraction may include a nutrient level obtained from a sensor worn on a user's tooth. User activity profile 112 includes at least an element of user activity data. User activity data may include any of the user activity data as described above. User activity data may include a description of what user was doing before, during, or after a biological extraction was obtained. For example, user activity data may include a description that user was at a hatha yoga class when user's blood pressure was measured. In yet another non-limiting example, user activity data may indicate that user had meditated for twenty minutes before user's hormone levels were tested.

With continued reference to FIG. 5, at step 510 a computing device generates using fitness training data 124 wherein fitness training data 124 includes a plurality of activity profiles and a plurality of correlated fitness profiles, and using a classification algorithm 140, a fitness classifier wherein the fitness classifier 136 inputs activity profiles and outputs fitness profiles. Fitness classifier 136 may be generated utilizing any of the methods as described above in reference to FIGS. 1-4. Classification algorithm 140 includes any of the classification algorithm 140 as described above in reference to FIGS. 1-4. Generating fitness classifier 136 may include extracting from user activity profile 112 an activity descriptor relating to a biological extraction and inputting the biological extraction and the activity descriptor relating to the biological extraction into the fitness classifier 136. For example, activity descriptor may include a description of one or more activities or exercises that a user may participate in on a routine basis but that may have not been performed before, during, or after a biological extraction and as such may not qualify as an element of user activity data. Generating fitness classifier 136 may include retrieving a plurality of chronological user biological extractions from biological database 108, classifying the plurality of chronological user biological extractions to each contain a classification label wherein the classification label indicates that a biological extraction is within normal limits or not within normal limits, and inputting the plurality of biological extractions each containing a classification label into the fitness classifier 136. A plurality of chronological user biological extractions may include any of the chronological user biological extractions as described above in reference to FIG. 1. For instance and without limitation, a plurality of chronological user biological extractions may include a first biological extraction collected three months prior, a second biological extraction collected two months prior, and a third biological extraction collected one month prior. In an embodiment, a plurality of chronological user biological extractions may include a first biological extraction such as a fasting glucose level obtained before user engaged in any exercise, a second biological extraction such as a hair sample analyzed for heavy metals 1 week after the first biological extraction, and a third biological extraction such as a nutrient level obtained from a microchip embedded in user's mouth one day after the second biological extraction. In yet another non-limiting example, a plurality of chronological user biological extractions may include a first heart rate collected while user played tennis, a second heart rate collected on a second day while user played golf, and a third heart rate collected on a third day while user was resting.

With continued reference to FIG. 5, at step 515 a computing device calculates using a fitness classifier 136 a classification algorithm 140 utilizing a user activity profile 112 as an input and outputs a fitness profile utilizing a fitness training data 124. Classification algorithm 140 includes any of the classification algorithm 140 as described above in reference to FIGS. 1-4. Fitness classifier 136 may select one or more classification algorithm 140 based on expert input which may be stored in training database 132. Fitness profile includes any of the fitness profiles as described above in reference to FIGS. 1-4.

With continued reference to FIG. 5, at step 520 a computing device 104 selects using a selected fitness profile an activity training set 148 wherein the activity training set 148 includes a plurality of fitness profiles and a plurality of correlated fitness recommendations. Activity training set 148 may include any of the activity training set 148 as described above in reference to FIGS. 1-4. Selecting activity training set 148 may include classifying the fitness profile to contain an activity classification label containing an activity level and selecting an activity training set 148 as a function of the activity classification label containing the activity level. Activity classification label includes any of the activity classification labels as described above in reference to FIGS. 1-4. In an embodiment, computing device 104 may select an activity training set 148 contained within training database 132 that contains an activity level that matches activity classification label. In yet another non-limiting example, activity training set 148 contained within training database 132 may be organized according to activity level, whereby computing device 104 may select an activity training set 148 that contains an activity level that matches the activity level contained within an activity classification label. In yet another non-limiting example, computing device 104 may select an activity training set 148 from training database 132 based on expert input. Expert input may include any of the expert input as described above in reference to FIGS. 1-4.

With continued reference to FIG. 5, at step 525 a computing device generates using activity training set 148 and the selected fitness profile a feature learning algorithm 152 wherein the feature learning algorithm 152 inputs the selected fitness profile and outputs recommended exercise. Feature learning algorithm 152 may include any of the feature learning algorithm 152 as described above in reference to FIGS. 1-4. Feature learning algorithm 152 may include one or more supervised feature learning algorithm 152. Feature learning algorithm 152 may include one or more unsupervised feature learning algorithm 152. Unsupervised feature learning algorithm 152 may include a k-means clustering algorithm. Feature learning algorithm 152 outputs recommended exercise. Recommended exercise includes any of the recommended exercise as described above in reference to FIGS. 1-4.

With continued reference to FIG. 1, at step 530 a computing device identifies recommended exercise for a user utilizing a user activity profile 112. Computing device 104 may identify exercises contained within a user activity profile 112. For example, a user activity profile 112 may include a description of one or more exercises user may engage in such as spinning, hot yoga, racket ball, brisk walking, and the like. Computing device 104 may compare output recommended exercise to exercises contained within a user activity profile 112. For example, computing device 104 may determine that user activity profile 112 may include a description of working out on a stair master while a recommended exercise may include cardiovascular exercise. Computing device 104 may compare user activity profile 112 to recommended exercise and determine that exercising on a stair master is a form of cardiovascular exercise. Computing device 104 generates a recommended exercise instruction set. Recommended exercise instruction set includes any of the recommended exercise instruction sets as described above in reference to FIGS. 1-4. Computing device 104 transmits a recommended exercise instruction set to a remote device 116. Remote device 116 includes any of the remote device 116 as described above in reference to FIGS. 1-4. Recommended exercise instruction set may be transmitted utilizing any network methodology as described herein. Identifying recommended exercise includes identifying exercises containing user specific modifications. User specific modifications include any of the user specific modifications as described above. Identifying recommended exercise includes identifying non-recommended exercise for a user.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
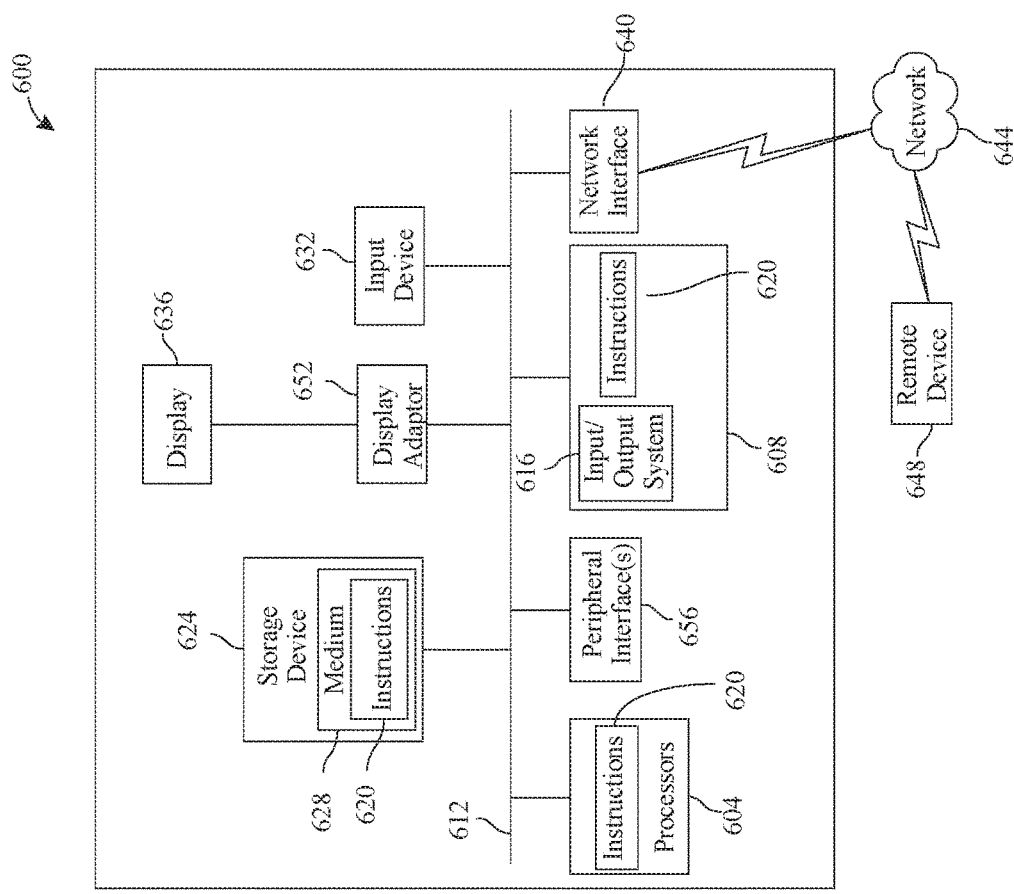
FIG. 6 is a block diagram of a computing system that can be used to implement any one or more of the methodologies disclosed herein and any one or more portions thereof. The drawings are not necessarily to scale and may be illustrated by phantom lines, diagrammatic representations and fragmentary views. In certain instances, details that are not necessary for an understanding of the embodiments or that render other details difficult to perceive may have been omitted.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Memory 608 may include various components (e.g., machine-readable media) including, but not limited to, a random access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIRE-WIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote device 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating fitness recommendations according to user activity profiles, the system comprising a computing device, the computing device further configured to: retrieve from a biological database a user activity profile wherein the user activity profile further comprises a biological extraction and at least an element of user activity data wherein the biological extraction further comprises at least an element of user physiological data;

generate a fitness classifier, wherein the fitness classifier comprises a machine-learning model trained by fitness training data comprising a plurality of activity profiles and a plurality of correlated fitness profiles, and a classification algorithm, wherein the fitness classifier is configured to receive activity profiles as inputs and outputs fitness profiles as a function of the fitness training data, and wherein generating the fitness classifier further comprises:
retrieving a plurality of chronological user biological extractions from the biological database;
classifying the plurality of chronological user biological extractions to a classification label wherein the classification label indicates that the biological extraction is within normal limits or not within normal limits; and inputting the plurality of biological extractions each containing a classification label into the fitness classifier;

determine a selected fitness profile, wherein determining the selected fitness profile further comprises inputting the user activity profile to the fitness classifier and outputting the selected fitness profile;

select, using the selected fitness profile, an activity training set wherein the activity training set includes a plurality of fitness profiles and a plurality of correlated fitness recommendations;

generate, a feature learning model, wherein the feature learning model comprises a machine-learning model trained by the activity training set, the selected fitness profile, and a feature learning algorithm wherein the feature learning model is configured to receive the selected fitness profile as inputs and outputs recommended exercise; and identify recommended exercises utilizing the user activity profile and the feature learning model.

2. The system of claim 1, wherein generating the fitness classifier further comprises: extracting from the user activity profile an activity descriptor relating to the biological extraction; and inputting the biological extraction and the activity descriptor relating to the biological extraction into the fitness classifier.

3. The system of claim 1, wherein selecting the activity training set further comprises: classifying the fitness profile to contain an activity classification label containing an activity level; and selecting the activity training set as a function of the activity classification label containing the activity level.

4. The system of claim 1, wherein generating the feature learning algorithm further comprises generating a supervised feature learning algorithm.

5. The system of claim 1, wherein generating the feature learning algorithm further comprises generating an unsupervised feature learning algorithm.

6. The system of claim 5, wherein the unsupervised feature learning algorithm further comprises a k-means clustering algorithm.

7. The system of claim 1, wherein identifying recommended exercises for the user further comprises:

identifying exercises contained within the user activity profile;

comparing the recommended exercises to the exercises contained within the user activity profile;

generating a recommended exercise instruction set; and transmitting the recommended exercise instruction set to a remote device.

8. The system of claim 1, wherein identifying recommended exercises for the user further comprises identifying exercises containing user specific modifications.

9. The system of claim 1, wherein identifying recommended exercises for the user further comprises identifying non-recommended exercises for the user.

10. A method of generating fitness recommendations according to user activity profiles, the method comprising:

retrieving, by a processor from a biological database a user activity profile wherein the user activity profile further comprises a biological extraction and at least an element of user activity data wherein the biological extraction further comprises at least an element of user physiological data;

generating, by the processor a fitness classifier, wherein the fitness classifier comprises a machine-learning model trained by fitness training data comprising a plurality of activity profiles and a plurality of correlated fitness profiles, and a classification algorithm, wherein the fitness classifier is configured to receive activity profiles as inputs and outputs fitness profiles as a function of the fitness training data, and wherein generating the fitness classifier further comprises:

retrieving a plurality of chronological user biological extractions from the biological database;

classifying the plurality of chronological user biological extractions to a classification label wherein the classification label indicates that the biological extraction is within normal limits or not within normal limits; and inputting the plurality of biological extractions each containing a classification label into the fitness classifier;

determining, by the processor a selected fitness profile, wherein determining the selected fitness profile further comprises inputting the user activity profile to the fitness classifier and outputting the selected fitness profile;

selecting, by the processor using the selected fitness profile, an activity training set wherein the activity training set includes a plurality of fitness profiles and a plurality of correlated fitness recommendations;

generating, by the processor a feature learning model, wherein the feature learning model comprises a machine-learning model trained by the activity training set, the selected fitness profile, and a feature learning algorithm wherein the feature learning model is configured to receive the selected fitness profile as inputs and outputs recommended exercise; and identifying, by the processor recommended exercises utilizing the user activity profile and the feature learning model.

11. The method of claim 10, wherein generating the fitness classifier further comprises: extracting from the user activity profile an activity descriptor relating to the biological extraction; and inputting the biological extraction and the activity descriptor relating to the biological extraction into the fitness classifier.

12. The method of claim 10, wherein selecting the activity training set further comprises: classifying the fitness profile to contain an activity classification label containing an activity level; and selecting the activity training set as a function of the activity classification label containing the activity level.

13. The method of claim 10, wherein generating the feature learning algorithm further comprises generating a supervised feature learning algorithm.

14. The method of claim 10, wherein generating the feature learning algorithm further comprises generating an unsupervised feature learning algorithm.

15. The method of claim 14, wherein generating the unsupervised feature learning algorithm further comprises generating a k-means clustering algorithm.

16. The method of claim 10, wherein identifying recommended exercises for the user further comprises:

identifying exercises contained within the user activity profile;

comparing the recommended exercises to the exercises contained within the user activity profile;
generating a recommended exercise instruction set; and
transmitting the recommended exercise instruction set to a remote device.

17. The method of claim 10, wherein identifying recommended exercises for the user further comprises identifying exercises containing user specific modifications.

18. The method of claim 10, wherein identifying recommended exercises for the user further comprises identifying non-recommended exercises for the user.

* * * * *